(12) United States Patent
Komata et al.

(10) Patent No.: US 7,115,771 B2
(45) Date of Patent: Oct. 3, 2006

(54) PROCESS FOR PRODUCING FLUORINE-CONTAINING ALKYLSULFONYLAMINOETHYL α-SUBSTITUTED ACRYLATE

(75) Inventors: Takeo Komata, Saitama (JP); Ryo Nadano, Saitama (JP); Makoto Matsuura, Saitama (JP)

(73) Assignee: Central Glass Company, Limited, Yamaguchi (JP)

( * ) Notice: Subject to any disclaimer, the term of this patent is extended or adjusted under 35 U.S.C. 154(b) by 0 days.

(21) Appl. No.: 11/068,824

(22) Filed: Mar. 2, 2005

(65) Prior Publication Data

US 2005/0240052 A1 Oct. 27, 2005

(30) Foreign Application Priority Data

Mar. 2, 2004 (JP) ............... P.2004-057390

(51) Int. Cl.
*C07C 69/52* (2006.01)
(52) U.S. Cl. .................................... 560/222
(58) Field of Classification Search .............. None
See application file for complete search history.

(56) References Cited

U.S. PATENT DOCUMENTS 6,165,678 A    12/2000  Allen et al.
6,949,325 B1 *  9/2005  Li et al. ............... 430/270.1

OTHER PUBLICATIONS

Narain et al, Macromolecules, Direct Synthesis and Aqueous Solution Properties of Well-Defined Cyclic Sugar Methacrylate Polymers, 2003, 36, pp. 4675-4678.*
Miraballes-Martinez, "Synthesis of Latex Particles with Surface Amino Groups", Journal of Polymer Science: Part A: Polymer Chemistry, 2000, vol. 38, pp. 4230-4237.
Korshunov et al., "α,β-Unsaturated Esters with Functional Substituents in the Alkoxy Group VI. Reactions of Amino- and (Alkylamino)-Alkanols with Acrylic and Methacrylic Esters and Acid Chlorides", Zhurnal Organicheskoi Khimii, Feb. 1969, vol. 5, No. 2, pp. 254-262.

* cited by examiner

Primary Examiner—Paul A. Zucker
(74) Attorney, Agent, or Firm—Young & Thompson

(57) ABSTRACT

The present invention provides a process for producing a fluorine-containing alkylsulfonylaminoethyl α-substituted acrylate represented by general formula [3]:

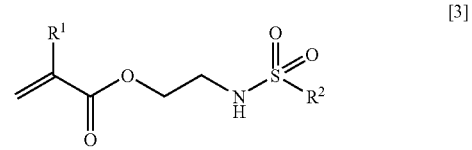

which comprises reacting an aminoethyl α-substituted acrylate represented by general formula [1a] or a salt thereof:

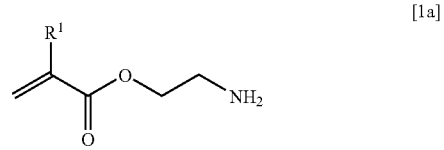

with a fluorine-containing alkylsulfonyl halide represented by general formula [2a] or a fluorine-containing alkylsulfonic anhydride represented by general formula [2b]:

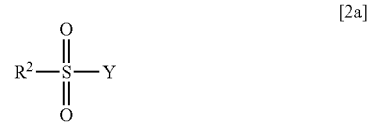

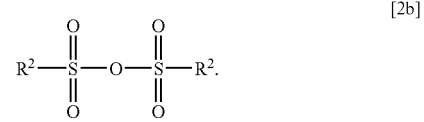

15 Claims, No Drawings

PROCESS FOR PRODUCING FLUORINE-CONTAINING ALKYLSULFONYLAMINOETHYL α-SUBSTITUTED ACRYLATE

FIELD OF THE INVENTION

The present invention relates to a process for producing a fluorine-containing alkylsulfonylaminoethyl α-substituted acrylate represented by the below-shown general formula [3], which is a useful compound as a monomer for a next-generation photoresist:

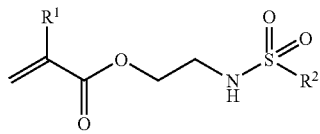

[3]

wherein $R^1$ is a hydrogen atom, a methyl group, an ethyl group, an n-propyl group, an isopropyl group, an n-butyl group, a sec-butyl group, a tert-butyl group, a fluoromethyl group, a difluoromethyl group, a trifluoromethyl group or a perfluoroethyl group; and $R^2$ is a fluorine-containing alkyl group such as a fluoromethyl group, a difluoromethyl group, a trifluoromethyl group, a perfluoroethyl group, an n-perfluoropropyl group or an n-perfluorobutyl group.

BACKGROUND OF THE INVENTION

Sulfonylaminoethyl α-substituted acrylates are promising compounds as monomers for next-generation photoresist materials, and resists containing the monomers as constituent elements are known to be excellent in light transparency and surface adsorptivity (see, for example, U.S. Pat. No. 6,165,678, which is hereinafter referred to as "Patent Document 1").

In Patent Document 1, there is no detailed description concerning the synthesis of the fluorine-containing alkylsulfonylaminoethyl α-substituted acrylate represented by the above-shown general formula [3] which is an objective compound of the invention, and the document merely discloses that sulfonylaminoethyl α-substituted acrylates in a broad sense can be synthesized by condensation of the corresponding sulfonylaminoethanol with α-substituted acryloyl chloride.

The process of Patent Document 1 mentioned above is a general process for manufacturing an α-substituted acrylic ester but there is no description therein concerning the synthesis of sulfonylaminoethyl α-substituted acrylates wherein $R^2$ is a fluorine-containing alkyl group such as a fluoromethyl group, a difluoromethyl group, a trifluoromethyl group, a perfluoroethyl group, an n-perfluoropropyl group, or an n-perfluorobutyl group.

According to the process of Patent Document 1, it can be presumed that the fluorine-containing alkylsulfonylaminoethyl α-substituted acrylate represented by the above-shown general formula [3] which is an object of the invention may be produced by reacting an α-substituted acryloyl chloride represented by general formula [4]:

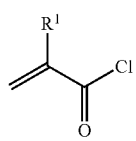

[4]

wherein the meaning of $R^1$ is the same as that defined above, with a fluorine-containing alkylsulfonylamino ethanol represented by general formula [5]:

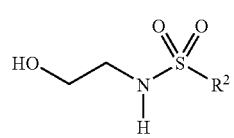

[5]

wherein the meaning of $R^2$ is the same as that defined above. At first, it was considered that the fluorine-containing alkylsulfonylamino ethanol represented by general formula [5] could be synthesized by reacting (through sulfonamidation reaction) aminoethanol represented by the formula [6a]:

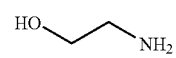

[6a]

or a salt of aminoethanol represented by the formula [6b]:

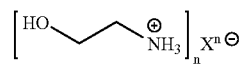

[6b]

wherein $X^{n-}$ is a counter anion (such as a fluoride ion, a chloride ion, a bromide ion, an iodide ion, a perchlorate ion, a perbromate, a hydrogen sulfate ion, or a sulfate ion) and n is a positive integer, with a fluorine-containing alkylsulfonyl halide represented by general formula [2a]:

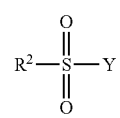

[2a]

or a fluorine-containing alkylsulfonic anhydride represented by general formula [2b]:

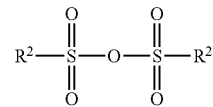

[2b]

wherein, in the formulae [2a] and [2b], the meaning of $R^2$ is the same as that defined above, and Y is a fluorine atom, a chlorine atom or a bromine atom.

However, the studies made by the present inventors revealed that in the case of a substrate wherein $R^2$ is a fluorine-containing alkyl group, which is a target of the invention, the sulfonamidation does not satisfactorily proceed and the formation of the fluorine-containing alkylsulfonylaminoethanol is not ascertained. Specifically, even when reaction temperature and time sufficient for promoting the reaction are applied, the presence of the fluorine-containing alkylsulfonylaminoethanol in the reaction mixture was not confirmed by gas chromatography of the substrate excluding a solvent (see Comparative Example 1). The fact that the fluorine-containing alkylsulfonylaminoethanol is not obtained in a sufficient yield gives serious influences from economic and operational viewpoints on the production of the fluorine-containing alkylsulfonylaminoethyl α-substituted acrylate represented by general formula [3] which is a final objective compound of the invention.

Thus, it is difficult to efficiently synthesize the fluorine-containing alkylsulfonylaminoethyl α-substituted acrylates based on the conventional technology and hence it is a problem to find out a process for producing the same in more reliable manner.

SUMMARY OF THE INVENTION

In consideration of the foregoing problems in the conventional art, the present inventors have extensively studied a process for producing the fluorine-containing alkylsulfonylaminoethyl α-substituted acrylate in order to establish a process suitable for the production in an industrial scale.

As a result, they have found that when an α-substituted acryloyl halide represented by general formula [7]:

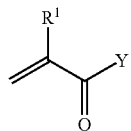

[7]

(wherein the meanings of $R^1$ and Y are the same as those defined for formulae [2a] and [2b])

is reacted with a salt of aminoethanol represented by the formula [6b]:

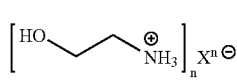

[6b]

(wherein $X^{n-}$ is a counter anion, wherein n is a positive integer), esterification proceeds in a high yield and a salt of an aminoethyl α-substituted acrylate represented by general formula [1b]:

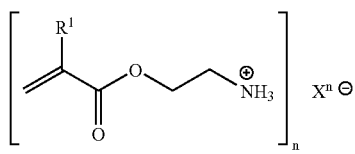

[1b]

(wherein the meanings of $R^1$ and $X^{n-}$ are the same as those defined above)

is obtained (a first step). It has been also found that the resulting salt of the aminoethyl α-substituted acrylate is highly stable and easy to purify and it is easy to enhance the purity by subjecting the salt in this form to a purification operation.

Moreover, they have found that when the salt of the aminoethyl α-substituted acrylate, or an aminoethyl α-substituted acrylate represented by general formula [1a] that is obtained by neutralizing the salt of the aminoethyl α-substituted acrylate with a base:

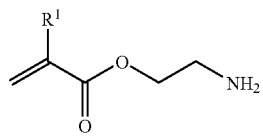

[1a]

(wherein the meaning of $R^1$ is the same as that defined above)

is reacted with a fluorine-containing alkylsulfonyl halide represented by general formula [2a] or a fluorine-containing alkylsulfonic anhydride represented by general formula [2b]:

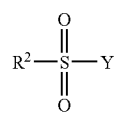

[2a]

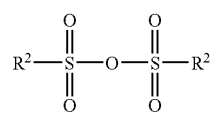

[2b]

(wherein the meanings of $R^2$ and Y are the same as those defined above), then an objective fluorine-containing alkylsulfonylaminoethyl α-substituted acrylate represented by general formula [3] is obtained smoothly (a second step).

The present inventors have further found that when these reactions are carried out under specific conditions, a particularly efficient amidation occurs to afford the objective fluorine-containing alkylsulfonylaminoethyl α-substituted acrylate represented by general formula [3] in a high yield. Thus, they have accomplished the invention.

According to the invention, the objective fluorine-containing alkylsulfonylaminoethyl α-substituted acrylates can be obtained in an extraordinary high yield as compared with the conventional art and also smoothly. Therefore, the invention provides an extremely excellent process for industrially producing the fluorine-containing alkylsulfonylaminoethyl α-substituted acrylate represented by general formula [3].

The process of the invention is summarized in Scheme 1.

Scheme 1

First Step

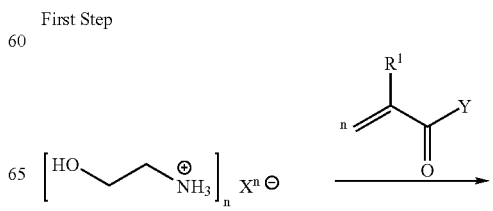

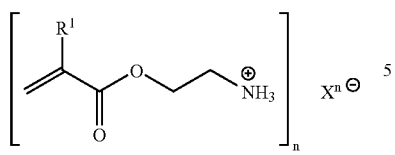

Second Step

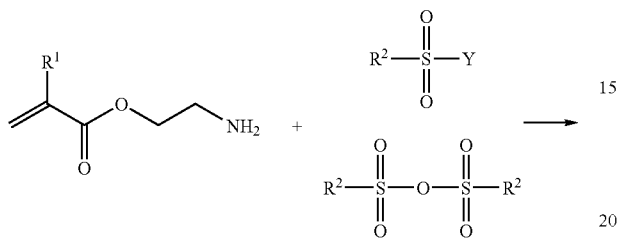

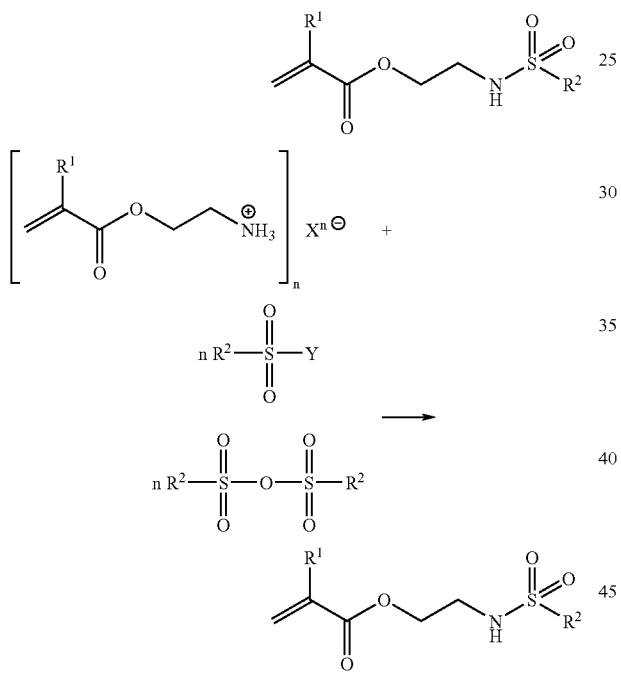

Specifically, the present invention provides the following processes.

(1) A process for producing a fluorine-containing alkylsulfonylaminoethyl α-substituted acrylate represented by general formula [3]:

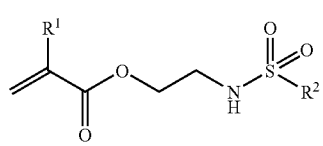

which comprises reacting an aminoethyl α-substituted acrylate represented by general formula [1a]:

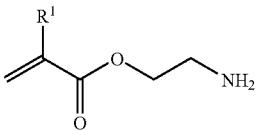

with a fluorine-containing alkylsulfonyl halide represented by general formula [2a] or a fluorine-containing alkylsulfonic anhydride represented by general formula [2b]:

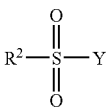

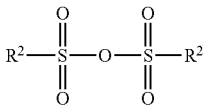

or reacting a salt of an aminoethyl α-substituted acrylate represented by general formula [1b]:

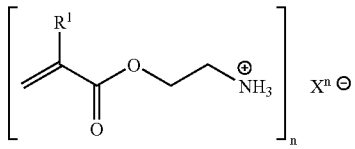

with a fluorine-containing alkylsulfonyl halide represented by general formula [2a] or a fluorine-containing alkylsulfonic anhydride represented by general formula [2b] in the presence of a base, wherein $R^1$ is a hydrogen atom, a methyl group, an ethyl group, an n-propyl group, an isopropyl group, an n-butyl group, a sec-butyl group, a tert-butyl group, a fluoromethyl group, a difluoromethyl group, a trifluoromethyl group, or a perfluoroethyl group; $R^2$ is a fluorine-containing alkyl group, such as a fluoromethyl group, a difluoromethyl group, a trifluoromethyl group, a perfluoroethyl group, an n-perfluoropropyl group or an n-perfluorobutyl group; $X^{n-}$ is a counter anion, wherein n is a positive integer; and Y is a fluorine atom, a chlorine atom or a bromine atom.

(2) The process according to item (1) above, wherein the sulfonamidation reaction is carried out by reacting the salt of the aminoethyl α-substituted acrylate represented by general formula [1b] with the fluorine-containing alkylsulfonyl halide represented by general formula [2a] or the fluorine-containing alkylsulfonic anhydride represented by general formula [2b] in the presence of a base.

(3) The process according to item (1) or (2) above, wherein the salt of the aminoethyl α-substituted acrylate represented by general formula [1b] is obtained by reacting an α-substituted acryloyl halide represented by general formula [7]:

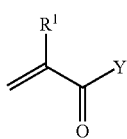

with a salt of aminoethanol represented by general formula [6b]:

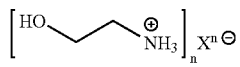

wherein $R^1$, $X^{n-}$, n and Y have the same meaning as defined above, respectively.

(4) The process according to item (1) above, wherein the aminoethyl α-substituted acrylate represented by general formula [1a] is obtained by reacting an α-substituted acryloyl halide represented by general formula [7]:

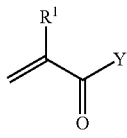

with a salt of aminoethanol represented by general formula [6b]:

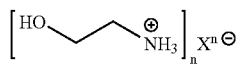

to obtain a salt of an aminoethyl α-substituted acrylate represented by general formula [1b]:

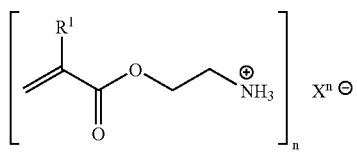

and then neutralizing the salt of the aminoethyl α-substituted acrylate with a base, wherein $R^1$, $X^{n-}$, n and Y have the same meaning as defined above, respectively.

(5) The process according to any one of items (1) to (4) above, wherein $R^2$ is a trifluoromethyl group.

(6) The process according to any one of items (1) to (5) above, wherein $R^1$ is a group selected from the group consisting of a hydrogen atom, a methyl group, an ethyl group, an n-propyl group, and an isopropyl group.

(7) The process according to any one of items (1) to (4) above, wherein $R^1$ is a methyl group.

(8) The process according to any one of items (1) to (4) above, wherein $R^1$ is a methyl group and $R^2$ is a trifluoromethyl group.

(9) The process according to any one of items (1) to (8) above, wherein Y is a fluorine atom or a chlorine atom.

(10) The process according to any one of items (1) to (9) above, wherein the sulfonamidation reaction is carried out at a temperature of from −50° C. to 30° C.

(11) The process according to any one of items (1) to (10) above, wherein the base to be used in the reaction of the salt of the aminoethyl α-substituted acrylate with the fluorine-containing alkylsulfonyl halide or the fluorine-containing alkylsulfonic anhydride is at least one base selected from the group consisting of trimethylamine, triethylamine, N,N-diethylmethylamine, tripropylamine, tributylamine, pyridine, 2,6-dimethylpyridine, dimethylaminopyridine, sodium carbonate, potassium carbonate, sodium hydroxide, and potassium hydroxide.

(12) The process according to any one of item (1) to (11) above, wherein the sulfonamidation reaction is carried out using at least one solvent selected from the group consisting of acetonitrile, dimethylformamide, dimethylacetamide, dimethyl sulfoxide, dimethylimidazolidinone, tetrahydrofuran, triethylamine, and pyridine.

(13) The process according to any one of items (1) to (12) above, wherein the sulfonamidation reaction is carried out using a polymerization inhibitor.

(14) The process according to item (13), wherein the polymerization inhibitor is at least one compound selected from the group consisting of hydroquinone, Methoquinone, 2,5-di-t-butylhydroquinone, 1,2,4-trihydroxybenzene, 2,5-bistetramethylbutylhydroquinone, leukoquinizarin, Nonflex F, Nonflex H, Nonflex DCD, Nonflex MBP, Ozonone 35, phenothiazine, tetraethylthiuram disulfide, 1,1-diphenyl-2-picrylhydrazyl, 1,1-diphenyl-2-picrylhydrazine, Q-1300, and Q-1301.

According to the invention, the objective fluorine-containing alkylsulfonylaminoethyl α-substituted acrylates can be produced in an extraordinary high yield as compared with the conventional art. Therefore, the invention provides an extremely excellent process for producing a fluorine-containing alkylsulfonylaminoethyl α-substituted acrylate in an industrial scale.

DETAILED DESCRIPTION OF THE INVENTION

The following will describe the invention in more detail. The invention relates to the first step (synthesis of the salt of the aminoethyl α-substituted acrylate) and the second step (synthesis of the fluorine-containing alkylsulfonylaminoethyl α-substituted acrylate). The process of the invention essentially comprises the second step and, optionally, further comprises the first step.

The substituent $R^1$ in the objective compound represented by general formula [3] which is a target of the present reaction is a hydrogen atom, a methyl group, an ethyl group, an n-propyl group, an isopropyl group, an n-butyl group, a sec-butyl group, a tert-butyl group, a fluoromethyl group, a difluoromethyl group, a trifluoromethyl group, or a perfluoroethyl group. Moreover, $R^2$ is a fluorine-containing alkyl group such as a fluoromethyl group, a difluoromethyl group, a trifluoromethyl group, a perfluoroethyl group, an n-perfluoropropyl group, or an n-perfluorobutyl group. The compounds represented by general formulae [1a], [1b], [2a],

[2b], and [7] as the starting materials may be selected depending on the kinds of $R^1$ and $R^2$ in the fluorine-containing alkylsulfonylaminoethyl α-substituted acrylate which is an objective compound.

In the invention, in view of the usefulness of the products, $R^2$ is particularly preferably a trifluoromethyl group. $R^1$ is particularly preferably a hydrogen atom, a methyl group, an ethyl group, an n-propyl group, and an isopropyl group. Of these, it is particularly preferred that $R^1$ is a methyl group and $R^2$ is a trifluoromethyl group.

Moreover, the counter anion $X^{n-}$ in general formulae [6b] and [1b] is not particularly limited as far as it is an inert ion which does not affect the reactions and n is 1, 2, or 3. Particularly preferred is a monovalent or divalent anion and examples thereof include fluoride ions, chloride ions, bromide ions, iodide ions, perchlorate ions, perbromate ions, hydrogen sulfate ions, sulfate ions, phosphate ions, and the like.

Each reaction step (the first step and the second step) of the invention can be carried out in a batch-type reaction apparatus. The following will describe the conditions thereof but does not intend to exclude any change of the reaction conditions in each apparatus of such an extent that those skilled in the art can easily control.

First, the first step will be described. The first step is a step of synthesizing a salt of an aminoethyl α-substituted acrylate represented by general formula [1a] by reacting an α-substituted acryloyl halide represented by general formula [7] with a salt of aminoethanol represented by general formula [6b]. This reaction may be carried out in accordance with the method and conditions described in J. Polymer Science A 35, 4230 (2000) or Zh Org Khim 5, 254 (1969). The following will describe preferable conditions on the substrate which is a subject of the invention in detail.

The amount of the α-substituted acryloyl halide to be used in the reaction of the first step is usually from 0.8 to 3.0 mol, preferably from 0.9 to 2.0 mol, more preferably from 1.0 to 1.5 mol per 1.0 mol of the salt of aminoethanol. When the amount of the α-substituted acryloyl halide is less than 0.8 mol per 1.0 mol of the salt of aminoethanol, the yield of the objective compound decreases. When it exceeds 3.0 mol, the α-substituted acryloyl halide which does not participate in the reaction increases and hence the case is economically not preferred in view of efforts and costs for disposal thereof.

In this reaction, the starting salt of aminoethanol represented by the formula [6b] is solid. Therefore, in order to improve operability, it is preferable to use a solvent in the reaction of the first step. The solvent usable is not particularly limited but preferred is at least one compound selected from aromatic hydrocarbon solvents such as benzene, toluene, and xylene; halogenated solvents such as methylene chloride, chloroform, and carbon tetrachloride; ether solvents such as diethyl ether, diisopropyl ether, dibutyl ether, and tetrahydrofuran; pentane, hexane, and heptane. Of these, particularly preferred are aromatic hydrocarbon solvents such as benzene, toluene and xylene, or halogenated solvents such as methylene chloride, chloroform and carbon tetrachloride.

The amount of the solvent to be used in the reaction is usually from 0.5 to 100 g, preferably from 1 to 20 g, more preferably from 2 to 10 g per 1 g of the salt of aminoethanol. When the amount of the solvent is less than 0.5 g per 1 g of the salt of aminoethanol, the concentration of slurry during the reaction is too high and hence operability lowers. When it exceeds 100 g, the case is economically not preferred in view of productivity.

The reaction temperature at the time when the reaction in the first step is carried out is usually from 20 to 200° C., preferably from 60 to 150° C., more preferably from 90 to 130° C. When the temperature is lower than 20° C., the reaction rate is extremely low and hence the production process cannot be practical. Moreover, when it exceeds 200° C., the starting α-substituted acryloyl chloride or the product salt of the aminoethyl α-substituted acrylate is apt to decompose and hence the case is not preferred.

The α-substituted acryloyl halide and salt of the aminoethanol to be used as reaction starting materials in the first step can be purchased as reagents for synthesis.

As a reactor for carrying out the reaction, preferred is one inside of which is lined with tetrafluoroethylene resin, chlorotrifluoroethylene resin, vinylidene fluoride resin, PFA resin, glass, or the like, a glass vessel, or one made of stainless.

The method for carrying out the reaction is not limited but one example of desirable embodiments is described in detail. A solvent and a salt of aminoethanol are weighed and charged into a reactor durable under reaction conditions and then heated with stirring. After the mixture reaches a constant temperature, a predetermined amount of an α-substituted acryloyl halide is added thereto. It is preferable to confirm the completion of the reaction by monitoring the consumption of the starting materials through sampling or the like.

The salt of the aminoethyl α-substituted acrylate represented by general formula [1b] obtained in the first step is highly stable and easy to purify. Therefore, it is particularly preferred that, after the completion of the reaction in the first step, the salt of the aminoethyl α-substituted acrylate represented by general formula [1b] is subjected to a purification step and the resulting highly pure salt of the aminoethyl α-substituted acrylate is provided as a starting material for the second step. The following will describe the purification step.

There is no limitation on the purification method of the crude salt of the aminoethyl α-substituted acrylate obtained in the first step. However, since the salt of the aminoethyl α-substituted acrylate is hardly soluble in an ether solvent such as diethyl ether, diisopropyl ether, dibutyl ether or tetrahydrofuran, when the crude salt of the aminoethyl α-substituted acrylate obtained in the first step is washed with the ether solvent, excess of the α-substituted acryloyl halide which has remained in the reaction of the first step can be separated and removed. By collecting and drying the salt of the aminoethyl α-substituted acrylate after washing, a highly pure salt of the aminoethyl α-substituted acrylate can be obtained.

Moreover, by neutralizing the salt of the aminoethyl α-substituted acrylate (preferably, one purified by the above-explained purification step) with a base, it can be converted into the aminoethyl α-substituted acrylate represented by general formula [1a]. As the base, at least one compound selected from the group consisting of trimethylamine, triethylamine, N,N-diethylmethylamine, tripropylamine, tributylamine, pyridine, 2,6-dimethylpyridine, dimethylaminopyridine, sodium carbonate, potassium carbonate, sodium hydroxide and potassium hydroxide is preferably used. Of these, triethylamine is particularly preferred. Not only the salt represented by general formula [1b] but also the free aminoethyl α-substituted acrylate represented by general formula [1a] thus obtained can be suitably used as a starting material for the second step.

Next, the second step will be described. The second step is a step of synthesizing a fluorine-containing alkylsulfonylaminoethyl α-substituted acrylate represented by general formula [3], which is an objective compound of the invention, by reacting a free aminoethyl α-substituted acrylate represented by general formula [1a] or a salt of an aminoethyl α-substituted acrylate represented by general formula [1b] with a fluorine-containing alkylsulfonyl halide represented by general formula [2a] or a fluorine-containing alkylsulfonic anhydride represented by general formula [2b].

The substituent $R^1$ in the aminoethyl α-substituted acrylate or salt thereof represented by general formula [1a] or [1b] which is a starting material to be used in the second step is, as mentioned above, a hydrogen atom, a methyl group, an ethyl group, an n-propyl group, an isopropyl group, an n-butyl group, a sec-butyl group, a tert-butyl group, a fluoromethyl group, a difluoromethyl group, a trifluoromethyl group or a perfluoroethyl group, and $X^{n-}$ is a counter anion as mentioned above. It is particularly preferred that they are those produced by the above-described method of the first step since they are economical and highly pure.

Of the fluorine-containing alkylsulfonyl halides to be used as another starting material for use in the second step, a perfluoroalkylsulfonyl fluoride (which is the case where Y in general formula [2a] is a fluorine atom) can be obtained by electrolytic fluorination of the corresponding alkylsulfonyl fluoride (see "Compounds of Fluorine (Fusso no Kagoubutsu)", 76, (1979, Kodansha Scientific)). Of the fluorine-containing alkylsulfonyl halides, a perfluoroalkylsulfonyl chloride (which is the case where Y in general formula [2a] is a chlorine atom) can be obtained by chlorinating, with phosphorus pentachloride, a perfluoroalkylsulfonic acid obtained by hydrolysis of a perfluoroalkylsulfonyl fluoride (see JP 11-236365 A).

At the reaction of the second step, in the case where the free aminoethyl α-substituted acrylate represented by general formula [1a] is used as a starting material, progress of the reaction is observed even when a base is not present but the reaction is preferably carried out in the presence of a base. As the base, at least one compound selected from the group consisting of trimethylamine, triethylamine, N,N-diethylmethylamine, tripropylamine, tributylamine, pyridine, 2,6-dimethylpyridine, dimethylaminopyridine, sodium carbonate, potassium carbonate, sodium hydroxide and potassium hydroxide is preferably used. Of these, triethylamine is particularly preferred.

Moreover, in the case where the salt of the aminoethyl α-substituted acrylate represented by general formula [1b] is used as a starting material in the reaction of the invention, the use of a base is necessary. As the base, at least one compound selected from the group consisting of trimethylamine, triethylamine, N,N-diethylmethylamine, tripropylamine, tributylamine, pyridine, 2,6-dimethylpyridine, dimethylaminopyridine, sodium carbonate, potassium carbonate, sodium hydroxide and potassium hydroxide is preferably used. Of these, triethylamine is particularly preferred.

In the case where the aminoethyl α-substituted acrylate represented by general formula [1a] is used as a starting material, the amount of the base to be used is usually from 0.2 to 15.0 mol, preferably from 0.5 to 10.0 mol, more preferably from 1.0 to 3.0 mol per 1.0 mol of the substrate aminoethyl α-substituted acrylate. When the amount of the base is less than 0.2 mol per 1.0 mol of the substrate aminoethyl α-substituted acrylate, both of the selectivity of the reaction and the yield of the objective compound decreases. When it exceeds 15.0 mol, the base which does not participate in the reaction increases and hence the case is economically not preferred. In the case that an inexpensive triethylamine or the like is used as a solvent, the amount may exceed 15.0 mol.

In the case that the salt of the aminoethyl α-substituted acrylate represented by general formula [1b] is used as a starting material in the reaction of the invention, the amount of the base to be used is usually from 0.5 to 30.0 mol, preferably from 0.8 to 15.0 mol, more preferably from 1.5 to 5.0 mol per 1.0 mol of the substrate salt of the aminoethyl α-substituted acrylate. When the amount of the base is less than 0.5 mol per 1.0 mol of the substrate salt of the aminoethyl α-substituted acrylate, both of the selectivity of the reaction and the yield of the objective compound decreases. When it exceeds 30.0 mol, the base which does not participate in the reaction increases and hence the case is economically not preferred. In the case that an inexpensive triethylamine or the like is used as a solvent, the amount may exceed 30.0 mol.

The amount of the fluorine-containing alkylsulfonyl halide or fluorine-containing alkylsulfonic anhydride to be used in the invention is usually from 0.2 to 3.0 mol, preferably from 0.5 to 1.5 mol, more preferably from 0.9 to 1.2 mol per 1.0 mol of the aminoethyl α-substituted acrylate or the salt of the aminoethyl α-substituted acrylate. When the amount of the fluorine-containing alkylsulfonyl halide or fluorine-containing alkylsulfonic anhydride is less than 0.2 mol per 1.0 mol of the aminoethyl α-substituted acrylate or the salt of the aminoethyl α-substituted acrylate, both of the selectivity of the reaction and the yield of the objective compound decreases. When it exceeds 3.0 mol, the fluorine-containing alkylsulfonyl halide or fluorine-containing alkylsulfonic anhydride which does not participate in the reaction increases and hence the case is economically not preferred in view of efforts and costs for disposal thereof. As mentioned above, the invention has a major advantage that the reaction smoothly proceeds without use of a large excess of any one reaction substrate. In order to take advantage of such a feature of the invention, the amount of the fluorine-containing alkylsulfonyl halide or fluorine-containing alkylsulfonic anhydride is preferably from 0.9 to 1.2 mol per 1.0 mol of the aminoethyl α-substituted acrylate or the salt of the aminoethyl α-substituted acrylate and in particular, it is desirable that the molar ratio of these components is close to 1:1.

In this reaction, the starting salt of the aminoethyl α-substituted acrylate is solid and after the reaction, a halogenate salt of the base precipitates as a by-product. Thus, in order to improve operability, it is preferable to use a solvent. The solvent usable is at least one compound selected from nitrile solvents such as acetonitrile and benzonitrile; amide solvents such as dimethylformamide, dimethylacetamide, and dimethylimidazolidinone; sulfoxide solvents such as dimethyl sulfoxide; ether solvents such as diethyl ether, diisopropyl ether, dibutyl ether, and tetrahydrofuran; basic solvents such as triethylamine and pyridine; halogenated solvents such as methylene chloride, chloroform, and carbon tetrachloride; aromatic hydrocarbon solvents such as benzene, toluene, and xylene; pentane, hexane, and heptane. Of these, nitrile solvents such as acetonitrile and benzonitrile; amide solvents such as dimethylformamide, dimethylacetamide, and dimethylimidazolidinone; sulfoxide solvents such as dimethyl sulfoxide; ether solvents such as diethyl ether, diisopropyl ether, dibutyl ether, and tetrahydrofuran; basic solvents such as triethylamine and pyridine are suitable.

The amount of the solvent to be used in the reaction is usually from 0.5 to 100 g, preferably from 1 to 20 g, more preferably from 2 to 10 g per 1 g of the aminoethyl α-substituted acrylate or the salt of the aminoethyl α-substituted acrylate. When the amount of the solvent is less than 0.5 g per 1 g of the aminoethyl α-substituted acrylate or the salt of the aminoethyl α-substituted acrylate, the slurry concentration of halogenate salt of the base precipitated during the reaction is too high and hence operability lowers. When it exceeds 100 g, the case is economically not preferred in view of productivity.

The reaction temperature at the time when the reaction is carried out is usually from −100 to 100° C., preferably from −70 to 50° C., more preferably from −50 to 30° C. When the temperature is lower than −100° C., the reaction rate is extremely low and hence the production process cannot be practical. Moreover, when it exceeds 100° C., the starting aminoethyl α-substituted acrylate or salt of the aminoethyl α-substituted acrylate, or the product fluorine-containing alkylsulfonylaminoethyl α-substituted acrylate is apt to polymerize and hence the case is not preferred.

In the reaction, for the purpose of preventing polymerization of the starting aminoethyl α-substituted acrylate or salt of the aminoethyl α-substituted acrylate or the produced fluorine-containing alkylsulfonylaminoethyl α-substituted acrylate, the reaction may be carried out in the presence of a polymerization inhibitor. The polymerization inhibitor to be used is preferably at least one compound selected from the group consisting of hydroquinone, Methoquinone, 2,5-di-t-butylhydroquinone, 1,2,4-trihydroxybenzene, 2,5-bistetramethylbutylhydroquinone, leukoquinizarin, Nonflex F, Nonflex H, Nonflex DCD, Nonflex MBP, Ozonone 35, phenothiazine, tetraethylthiuram disulfide, 1,1-diphenyl-2-picrylhydrazyl, 1,1-diphenyl-2-picrylhydrazine, Q-1300, and Q-1301. The above polymerization inhibitors are commercial products and are easily available.

The amount of the polymerization inhibitor to be used in the reaction is usually from 0.00001 to 0.1 mol, preferably from 0.00005 to 0.05 mol, more preferably from 0.0001 to 0.01 mol per 1.0 mol of the starting aminoethyl α-substituted acrylate or salt of the aminoethyl α-substituted acrylate. When the amount of the polymerization inhibitor exceeds 0.1 mol per 1.0 mol of the starting aminoethyl α-substituted acrylate or salt of the aminoethyl α-substituted acrylate, there is not a large difference in the ability of preventing the polymerization and hence the case is economically not preferred. When the amount of the polymerization inhibitor is less than 0.00001 mol, the effect of particular use of the inhibitor is hardly obtained.

As a reactor for carrying out the reaction, preferred is one inside of which is lined with tetrafluoroethylene resin, chlorotrifluoroethylene resin, vinylidene fluoride resin, PFA resin, glass, or the like, a glass vessel, or one made of stainless.

The method for carrying out the invention is not limited but one example of desirable embodiments is described in detail. A base, a solvent, a starting salt of an α-substituted acrylate and a polymerization inhibitor are added into a reactor durable under reaction conditions, and the mixture of the starting materials are cooled by means of a cooling medium with stirring. After the mixture reaches a constant temperature, a predetermined amount of a fluorine-containing alkylsulfonyl halide is added into the reaction mixture. It is preferable to confirm the completion of the reaction by monitoring the consumption of the starting materials through sampling or the like.

The fluorine-containing alkylsulfonylaminoethyl α-substituted acrylate represented by general formula [3] produced by the process of the invention are purified by applying known methods. For example, a crude organic matter is obtained by removing the reaction solvent by evaporation under reduced pressure, suspending the residue in a solvent such as diisopropyl ether, removing the precipitated hydrogen halide salt of the base by filtration, and then removing the solvent by evaporation. A highly pure fluorine-containing alkylsulfonylaminoethyl α-substituted acrylate can be obtained by subjecting the resulting crude organic matter to purification such as column chromatography, distillation, recrystallization, or the like.

EXAMPLES

The present invention will be illustrated in greater detail with reference to the following Examples, but the invention should not be construed as being limited thereto. Herein, the "%" in compositional analytic values means "area %" of organic components excluding solvent components, the values being obtained by sampling a part of the reaction mixture or the product, dissolving the organic component into diisopropyl ether, and measuring the solution by gas chromatography.

Example 1

In a 500 mL three-neck flask equipped with a thermometer and a reflux condenser were placed 300 g of toluene and 60.0 g (0.62 mol) of ethanolamine hydrochloride, followed by heating to 110° C. with stirring. After the inner temperature reached 110° C., 77.1 g (0.74 mol) of methacryloyl chloride was added dropwise thereto over a period of 30 minutes. After completion of the dropwise addition, the mixture was continued to stir for further 3 hours and then cooled to 0° C. with stirring. The precipitated solid was collected by filtration and then the resulting solid was washed with 300 g of diisopropyl ether. The solid was collected by filtration and then dried under reduced pressure to obtain 85.2 g of 2-aminoethyl 2-methylacrylate hydrochloride.

Example 2

In a 1 L three-neck flask equipped with a thermometer and a reflux condenser were placed 350 g of acetonitrile, 70.7 g (0.699 mol) of triethylamine, 33.1 g (0.200 mol) of 2-aminoethyl 2-methylacrylate hydrochloride, and 0.2 g of phenothiazine, followed by cooling to −30° C. with stirring. After the inner temperature reached −30° C., 36.5 g (0.240 mol) of trifluoromethanesulfonyl fluoride was introduced into the slurry as a gas over a period of 1 hour. After completion of the introduction, the mixture was continued to stir for further 1 hour and then warmed to room temperature. The solvent acetonitrile and unreacted trifluoromethanesulfonyl fluoride were removed by evaporation from the reaction solution under reduced pressure. One litter of diisopropyl ether was added thereto to form a suspension and the precipitated triethylamine hydrochloride and triethylamine hydrofluoride were removed by filtration. To the filtrate was added 200 mL of an 18% aqueous calcium chloride solution, followed by washing and separation into two layers. Furthermore, the organic layer was washed with 200 g of a 10% aqueous sodium chloride solution three times. The organic layer was dried over 40 g of magnesium sulfate. After removal of the magnesium sulfate by filtration, 0.2 g of phenothiazine was added thereto and the solvent was removed by evaporation to obtain 44.2 g of a crude organic matter. The crude organic matter was distilled under reduced pressure and a fraction of 105 to 115° C./13 Pa was collected, whereby 36.0 g of 2-{[(trifluoromethyl)sulfonyl]amino}ethyl 2-methylacrylate was obtained. Gas chromatographic investigation of composition thereof revealed that objective 2-{[(trifluoromethyl)sulfonyl]amino}ethyl 2-methylacrylate was 97.5%. The resulting organic matter was crystallized from diisopropyl ether/n-hexane to obtain 32.4 g of white crystals. Gas chromatographic investigation of composition thereof revealed that objective 2-{[(trifluoromethyl)sulfonyl]amino}ethyl 2-methylacrylate was 99.0%. The yield was 61.4%.

Melting point: 47 to 48° C.

$^1$H NMR (solvent: CDCl$_3$, standard substance: TMS); δ 6.16 (dq, J=0.98 Hz, J=1.22 Hz, 1H), 5.66 (dq, J=1.46 Hz, J=1.22 Hz, 1H), 4.32 (dd, J=5.12 Hz, J=1.71 Hz, 2H), 3.61 (dt, J=0.49 Hz, J=5.12 Hz, 2H), 1.96 (dd, J=0.98 Hz, J=1.46 Hz, 3H)

$^{19}$F NMR (solvent: CDCl$_3$, standard substance: CCl$_3$F); δ −77.97 (s, 3F).

Example 3

In a 1 L three-neck flask equipped with a thermometer and a reflux condenser were placed 350 g of acetonitrile, 70.7 g (0.699 mol) of triethylamine, 33.1 g (0.200 mol) of 2-aminoethyl 2-methylacrylate hydrochloride, and 0.2 g of phenothiazine, followed by cooling to −30° C. with stirring. After the inner temperature reached −30° C., 40.3 g (0.239 mol) of trifluoromethanesulfonyl chloride was introduced into the slurry as a gas over a period of 1 hour. After completion of the introduction, the mixture was continued to stir for further 1 hour and then warmed to room temperature. The solvent acetonitrile and unreacted trifluoromethanesulfonyl chloride were removed by evaporation from the reaction solution under reduced pressure. One litter of diisopropyl ether was added thereto to form a suspension and the precipitated triethylamine hydrochloride was removed by filtration. The filtrate was washed with 200 mg of a 10% aqueous sodium chloride solution three times. The organic layer was dried over 40 g of magnesium sulfate. After removal of the magnesium sulfate by filtration, 0.2 g of phenothiazine was added thereto and the solvent was removed by evaporation to obtain 22.5 g of a crude organic matter. The crude organic matter was distilled under reduced pressure and a fraction of 105 to 115° C./13 Pa was collected, whereby 9.9 g of 2-{[(trifluoromethyl)sulfonyl]amino}ethyl 2-methylacrylate was obtained. Gas chromatographic investigation of composition thereof revealed that objective 2-{[(trifluoromethyl)sulfonyl]amino}ethyl 2-methylacrylate was 98.0%. The yield was 18.6%.

Example 4

In a 200 mL three-neck flask equipped with a thermometer and a reflux condenser were placed 100 mL of acetonitrile, 13.5 g (0.13 mol) of triethylamine, 10.0 g (0.060 mol) of 2-aminoethyl 2-methylacrylate hydrochloride, and 0.05 g of phenothiazine, followed by cooling to −30° C. with stirring. After the inner temperature reached −30° C., 18.8 g (0.067 mol) of trifluoromethanesulfonic anhydride was added dropwise thereto over a period of 30 minutes and the mixture was continued to stir for further 1 hour and then warmed to room temperature. The solvent acetonitrile was removed by evaporation from the reaction solution under reduced pressure. Then, 150 mL of diisopropyl ether was added thereto and the mixture was washed with 100 mL of a 10% aqueous sodium chloride solution three times. The organic layer was dried over 10 g of magnesium sulfate. After removal of the magnesium sulfate by filtration, 0.05 g of phenothiazine was added thereto and the solvent was removed by evaporation to obtain 15 g of a crude organic matter. The crude organic matter was distilled under reduced pressure and a fraction of 105 to 115° C./13 Pa was collected, whereby 8.43 g of 2-{[(trifluoromethyl)sulfonyl]amino}ethyl 2-methylacrylate was obtained. Gas chromatographic investigation of composition thereof revealed that objective 2-{[(trifluoromethyl)sulfonyl]amino}ethyl 2-methylacrylate was 94.0%. The yield was 50.6%.

Comparative Example 1

In a 200 mL three-neck flask equipped with a thermometer and a reflux condenser were placed 50 mL of acetonitrile, 5.1 g (0.05 mol) of triethylamine, and 3.1 g (0.05 mol) of aminoethanol, followed by cooling to −40° C. with stirring. After the inner temperature reached −35° C., 9.12 g (0.06 mol) of trifluoromethanesulfonyl fluoride was introduced thereinto as a gas over a period of 1.5 hours. After completion of the introduction, the mixture was cooled for further 1.5 hours, continued to stir, and warmed to room temperature. The resulting reaction solution was analyzed by gas chromatography but no peak of the reaction product was observed. Then, hydrogen chloride gas was blown into the resultant mixture to convert the triethylamine into the corresponding hydrochloride salt and then gas chromatographic analysis was conducted. Similarly, however, no peak of the reaction product was similarly observed.

While the present invention has been described in detail and with reference to specific embodiments thereof, it will be apparent to one skilled in the art that various changes and modifications can be made therein without departing from the spirit and scope thereof.

The present application is based on Japanese Patent Application No. 2004-057930 filed Mar. 2, 2005, the contents thereof being herein incorporated by reference.

What is claimed is:

1. A process for producing a fluorine-containing alkylsulfonylaminoethyl α-substituted acrylate represented by general formula [3]:

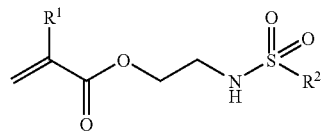

which comprises reacting an aminoethyl α-substituted acrylate represented by general formula [1a]:

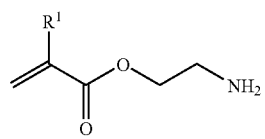

with a fluorine-containing alkylsulfonyl fluoride represented by general formula [2a] or a fluorine-containing alkylsulfonic anhydride represented by general formula [2b]:

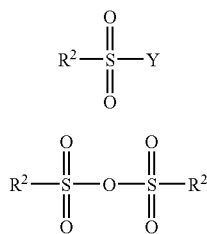

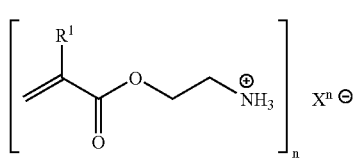

or reacting a salt of an aminoethyl α-substituted acrylate represented by general formula [1b]:

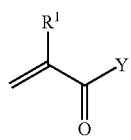

with a fluorine-containing alkylsulfonyl halide represented by general formula [2a] or a fluorine-containing alkylsulfonic anhydride represented by general formula [2b] in the presence of a base, wherein $R^1$ is a hydrogen atom, a methyl group, an ethyl group, an n-propyl group, an isopropyl group, an n-butyl group, a sec-butyl group, a tert-butyl group, a fluoromethyl group, a difluoromethyl group, a trifluoromethyl group, or a perfluoroethyl group; $R^2$ is a fluorine-containing alkyl group; $X^{n-}$ is a counter anion, wherein n is a positive integer; and Y is a fluorine atom.

2. The process according to claim 1, wherein the reaction is carried out by reacting the salt of the aminoethyl α-substituted acrylate represented by general formula [1b] with the fluorine-containing alkylsulfonyl fluoride represented by general formula [2a] or the fluorine-containing alkylsulfonic anhydride represented by general formula [2b] in the presence of a base.

3. The process according to claim 1, wherein the salt of the aminoethyl α-substituted acrylate represented by general formula [1b] is obtained by reacting an α-substituted acryloyl halide represented by general formula [7]:

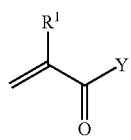

with a salt of aminoethanol represented by general formula [6b]:

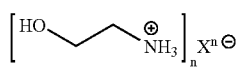

wherein $R^1$, $X^{n-}$, n and Y have the same meaning as defined above, respectively.

4. The process according to claim 1, wherein the aminoethyl α-substituted acrylate represented by general formula [1a] is obtained by reacting an α-substituted acryloyl halide represented by general formula [7]:

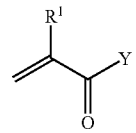

with a salt of aminoethanol represented by general formula [6b]:

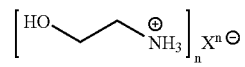

to obtain a salt of an aminoethyl α-substituted acrylate represented by general formula [1b]:

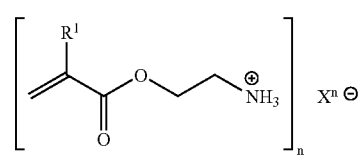

and then neutralizing the salt of the aminoethyl α-substituted acrylate with a base, wherein $R^1$, $X^{n-}$, n and Y have the same meaning as defined above, respectively.

5. The process according to claim 1, wherein $R^2$ is a trifluoromethyl group.

6. The process according to claim 1, wherein $R^1$ is a group selected from the group consisting of a hydrogen atom, a methyl group, an ethyl group, an n-propyl group, and an isopropyl group.

7. The process according to claim 1, wherein $R^1$ is a methyl group.

8. The process according to claim 1, wherein $R^1$ is a methyl group and $R^2$ is a trifluoromethyl group.

9. The process according to claim 1, wherein the reaction is carried out at a temperature of from −50° C. to 30° C.

10. The process according to claim 1, wherein the base to be used in the reaction of the salt of the aminoethyl α-substituted acrylate with the fluorine-containing alkylsulfonyl fluoride or the fluorine-containing alkylsulfonic anhydride is at least one base selected from the group consisting of trimethylamine, triethylamine, N,N-diethylmethylamine, tripropylamine, tributylamine, pyridine, 2,6-dimethylpyridine, dimethylaminopyridine, sodium carbonate, potassium carbonate, sodium hydroxide, and potassium hydroxide.

11. The process according to claim 1, wherein the reaction is carried out using at least one solvent selected from the group consisting of acetonitrile, dimethylformamide, dimethylacetamide, dimethyl sulfoxide, dimethylimidazolidinone, tetrahydrofuran, triethylamine, and pyridine.

12. The process according to claim 1, wherein the reaction is carried out using a polymerization inhibitor.

13. The process according to claim 12, wherein the polymerization inhibitor is at least one compound selected from the group consisting of hydroquinone, Methoquinone, 2,5-di-t-butylhydroquinone, 1,2,4-trihydroxybenzene, 2,5-bistetramethylbutylhydroquinone, leukoquinizarin, Nonflex F, Nonflex H, Nonflex DCD, Nonflex MBP, Ozonone 35, phenothiazine, tetraethylthiuram disulfide, 1,1-diphenyl-2-picrylhydrazyl, 1,1-diphenyl-2-picrylhydrazine, Q-1300, and Q-1301.

14. The process according to claim 1, wherein the aminoethyl α-substituted acrylate represented by general formula [1a] is reacted with the fluorine-containing alkylsulfonyl fluoride represented by general formula [2a].

15. The process according to claim 2, wherein the aminoethyl α-substituted acrylate represented by general formula [1a] is reacted with the fluorine-containing alkylsulfonyl fluoride represented by general formula [2a].

* * * * *